United States Patent [19]

Schulte

[11] Patent Number: 4,626,530

[45] Date of Patent: Dec. 2, 1986

[54] TREATMENT OF EYE INFLAMMATION WITH BIPHENAMINE

[76] Inventor: Thomas L. Schulte, 218 Family Farm Dr., Woodside, Calif. 94062

[21] Appl. No.: 697,101

[22] Filed: Feb. 1, 1985

Related U.S. Application Data

[63] Continuation-in-part of Ser. No. 517,417, Jan. 17, 1984, Pat. No. 4,497,824, and a continuation-in-part of Ser. No. 456,896, Jan. 10, 1983, Pat. No. 4,469,702, each is a continuation-in-part of Ser. No. 276,566, Jun. 23, 1981, Pat. No. 4,369,190.

[51] Int. Cl.$^4$ ............................................ A61K 31/615
[52] U.S. Cl. .................................................... 514/166
[58] Field of Search .......................................... 514/166

[56] References Cited

U.S. PATENT DOCUMENTS 3,551,554  8/1968  Hershler ............................. 514/166
4,073,897  2/1978  Karlor ................................ 514/166

Primary Examiner—Stanley J. Friedman
Attorney, Agent, or Firm—Millen & White

[57] ABSTRACT

Inflammation of the eye exposed to an irritant is prevented or ameliorated by applying thereto an aqueous solution of biphenamine, optionally in admixture with a skin penetrant such as DMSO.

10 Claims, No Drawings

TREATMENT OF EYE INFLAMMATION WITH BIPHENAMINE

This is a continuation-in-part of application Ser. No. 517,417, filed Jan. 17, 1984, now U.S. Pat. No. 4,497,824, and Ser. No. 456,896, filed Jan. 10, 1983, now U.S. Pat. No. 4,469,702, both filed as a continuation-in-part of application Ser. No. 276,566, filed June 23, 1981, now U.S. Pat. No. 4,369,190.

BACKGROUND OF THE INVENTION

This invention relates to a method for the prevention and treatment of eye inflammation due to exposure to an irritant.

It has long been known that eye irritation and inflammation can occur from exposure to a wide variety of chemical irritants, e.g., smog, building fires, tobacco smoke and industrial chemicals. More recently, contact lenses have become a major source of such eye irritation and inflammation. There are several non-prescription products marketed today to treat such eye ailments. However, some patients are sensitive to the chemicals in them, some do not respond thereto and none are reliably effective in preventing the irritation which often is associated with wearing contact lenses. The prescription drugs, such as antibiotics and steroidal anti-inflammatory agents, while generally more effective have their own disadvantages.

There therefore is a long standing need for safe and effective opthalmic anti-inflammatory agent for treating eye irritation, especially that associated with contact lens use. There is also a need for a non-toxic, non-allergenic bacteriostat and fungistat which is also effective in promoting the normal healing of the surface of the eye by suppressing infection and/or the natural inflammatory process. The present invention meets those needs.

The compositions employed in this invention comprise biphenamine ($\beta$-diethylaminoethyl 3-phenyl-2-hydroxybenzoate), either as the free base or a pharmaceutically acceptable acid addition salt thereof. Salts of this compound are known to have a variety of activities, including local anesthetic (U.S. Pat. No. 1,976,922); treatment of seborrhea capitis in a shampoo (U.S. Pat. No. 3,123,531); as well as antihistaminic and bactericidal activity and fungicidal properties (U.S. Pat. No. 2,593,350; Report Annual Meeting So. Med. Assoc., Nov. 6, 1961).

Biphenamine hydrochloride has been sold as a 1% ointment, under the trademark "Melsaphine," as a topical anesthetic agent possessing bactericidal, fungicidal and antihistamine properties and as a 1% aqueous shampoo under the trademark "Alvinine," Federal Register, Vol. 34, No. 189, page 153, Oct. 2, 1969. See also U.S. Pat. No. 3,123,531.

Although its use in a shampoo for treating seborrhea and related conditions is claimed in U.S. Pat. No. 3,123,531, nothing was known concerning its ability to prevent or ameliorate inflammation in eyes which are exposed to an irritant.

The topical compositions employed in the method of this invention preferably also comprise a small amount of a skin penetrant, e.g., DMSO (dimethyl sulfoxide) or polypropylene glycol, which has no anti-inflammatory effects in the eye at the concentration employed. U.S. Pat. No. 3,551,554 and 3,711,602 disclose that DMSO is effective as an agent for enhancing tissue penetration of physiologically active agents. U.S. Pat. No. 3,549,770 discloses (Example 36) the topical application of a mixture of acetylsalicylic acid and DMSO is more effective than DMSO alone to relieve the pain and muscle spasm of rheumatoid spondylitis. See also U.S. Pat. Nos. 3,711,602; 3,711,606; and 3,743,727 and references cited therein. These patents disclose that the tissue penetration of physiologically active compounds, inter alia, steroidal agents and certain antimicrobial agents, can be enhanced by DMSO. U.S. Pat. No. 3,740,420 discloses DMSO compositions for topical administration containing thickening agents.

The foregoing patents disclose that concentrations of DMSO of 10% by weight and above can effect penetration of such agents through various mucous membrane barriers and that concentrations of 50% by weight and above are effective to achieve penetration thereof through the skin. DMSO is also known to enhance the antiperspirant activity astringent of aluminum, zinc and zirconium salts (U.S. Pat. No. 3,499,961).

DMSO has been disclosed as useful for treating a variety of pathological conditions. U.S. Pat. No. 3,549,770 discloses topical application as a particularly advantageous route. This patent claims methods of relieving the signs and symptoms of tissue inflammation; of vascular insufficiency in the blood and lymph circulatory system; of respiratory distress; of arthritis and a method of promoting tissue repair, by administering an effective amount of DMSO, preferably topically. Dosages as low as 0.01 g/kg and up to 1.0 g/kg per day and sometimes higher dosages are contemplated with 0.1–0.2 g/kg individual doses being average. Higher concentrations of DMSO, such as at least 25% and more often at least about 50% are preferred for topical application. In one example (Example 27) the pain associated with skin abrasion was relieved with 15% DMSO in isotonic saline. 10% to 90% water solutions of DMSO, preferably 20% to 40%, in water, alcohol or glycerine are useful for topical application to the mucous membranes of the body although " . . . lower concentrations of DMSO say down to 3% by weight may be useful in some instances."

The use of DMSO as an ataratic agent is disclosed in U.S. Pat. No. 3,790,682. Pharmaceutical compositions containing DMSO and thickening agents are disclosed in U.S. Pat. No. 3,740,420, along with their use to treat and repair damaged tissue, as an anti-inflammatory agent, as an analgesic agent, as a muscle relaxant, as an agent for treating vascular insufficiency, and relieve the signs and symptoms of certain specific syndromes, viz., respiratory distress, arthritis and burns. None of the foregoing references disclose or suggest that the prevention and amelioration of eye inflammations can be achieved with low concentration of DMSO at concentrations below 10%, although U.S. Pat. No. 3,549,770 discloses (Col. 10, lines 42–49) that for pharyngitis or hiccups, the subject may gargle with a more dilute aqueous solution, e.g., containing 1% or preferably 10% by weight of DMSO, and (Col. 28, lines 44–56) that concentrations of DMSO down to 3% by weight may be useful in some instances, with 10% to 90% water solutions being particularly suitable. The use of DMSO in ophthalmic solutions at concentrations below 10% by weight is not suggested in the prior art. Moreover, low concentrations of DMSO or propylene glycol alone have little if any beneficial effect in treating eye inflammations.

SUMMARY OF THE INVENTION

In a method of use aspect, this invention relates to a method for preventing or ameliorating an inflammatory response in an eye exposed to an irritant, which comprises applying topically to the affected eye of the patient an anti-inflammatorily effective amount of biphenamine, as an opthomologically acceptable aqueous mixture comprising a pharmaceutically acceptable carrier.

DETAILED DISCUSSION

The aqueous mixture of a biphenamine (base or acid addition salt thereof) and optional skin penetrant is applied topically to the affected area as a solution in a pharmaceutically acceptable liquid carrier or diluent, preferably aqueous, e.g., in the form of clear solutions, such as drops, or in the form of lotions or other viscous aqueous liquids. The mixture can also be semi-solid, e.g., in the form of an ointment or cream. Viscosity regulating agents, such as thickeners and gelling agents, e.g., glycerin, ethylene glycol, sodium carboxymethylcellulose, etc., can also be used to regulate flowability. See U.S. Pat. Nos. 3,740,420 and 3,711,602, whose disclosures are incorproated herein by reference. Propylene glycol itself is useful as a viscosity raising agent. They can be in the form of an oil-in-water or water-in-oil emulsion, as disclosed in U.S. Pat. No. 3,740,420, or as a single phase aqueous solution, the latter being preferred. Organic solvents, e.g., ethanol or isopropanol, can also be present.

The skin penetrant generally is present in the mixture at relatively low concentrations, e.g., at least about 1%, which concentrations lack any significant topical anti-inflammatory activity in the eye in the absence of the biphenamine. DMSO is employed at concentrations of less than 10%, e.g., 3–7%, preferably about 5%. At these concentrations, DMSO exhibits none of the healing effects achieved when it is applied to the eye in admixture with biphenamine nor the side effects observed at higher concentrations. Propylene glycol is employed at concentrations of about 1% to 20%, preferably about 5% to 15%, more preferably about 10%. Propylene glycol has desirable emollient and thickening qualities, which therefore makes it preferable in some formulations and with some patients.

Although the biphenamine can be present in the mixture employed at any convenient concentration, generally concentrations of from about 0.05 to 0.5%, are employed. It preferably is present in the form of a pharmaceutically acceptable salt thereof, e.g., hydrochloride, hydrobromide, sulfate, phosphate, acetate, succinate, tartrate, benzoate, citrate, lactate or maleate, preferably the hydrochloride. Although acid addition salts of biphenamine are disclosed in U.S. Pat. No. 1,976,922 as having local anesthetic activity at a 2% concentration, neither its ability to promote healing when applied topically to inflammed eyes nor its effectiveness in the eye for any purpose at lower concentrations is suggested.

The biphenamine and optional skin penetrant are applied topically to the eye on successive occasions, e.g., as frequently as every hour or as infrequently as daily or longer, depending on the severity and intractability of the inflammatory condition. In the case of eye irritation due to contact lens, it is desirable to apply the aqueous mixture to the eye on successive occasions thereafter, e.g., once or twice daily for 2-14 days or longer until inflammation has been eliminated or when the irritant is a contact lens.

The amount of the aqueous mixture applied to the affected eye will depend on such factors as the degree of irritation, the concentration of biphenamine and skin penetrant therein and the individual's responsiveness to the therapy. One or two drops per application usually is effective. The mixture can be applied to the eye with an eye dropper or from a conventional squeeze bottle.

The compositions of this invention are also effective for the amelioration of the pain associated with the condition being treated. From clinical observations, when a composition of this invention is applied to the affected eye on successive occasions, not only is pain promptly ameliorated or eliminated, the healing process is facilitated, apparently by the suppression of the inflammatory response and/or associated infection.

The compositions of this invention are also useful for promoting the healing of a variety of pathological conditions of the skin, and other topically accessible areas of the body, e.g., those caused by viral, bacterial, fungal and other microorganisms infections or by localized inflammatory conditions, particularly those which produce a lesion in or a pathological thickening of the epithelium, e.g., scabs, tumorous tissue, e.g., herpes virus lesions, fungus infections of the perineum, feet, hands, ear canal, inflammation or sclerosis of the ear drum, urinary bladder, urethra, abscess cavities, leg ulcers, bed sores, infected sinuses, senile keratosis, animal and insect bites.

Although biphenamine hydrochloride as a 1% ointment is known to be useful for the treatment of minor burns, minor skin irritations or insect bites and to have bactericidal, fungicidal and antihistiminic properties at that concentration, it is surprising that concentrations thereof of only about 0.1% are effective in treating eye irritation. Although U.S. Pat. No. 2,594,350 teaches that a 0.14% solution of the mandelic acid salt of biphenamine is useful as a urinary antiseptic and germicide, the activity thereof is due in part to the known urinary bactericidal activity of mandelic acid.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The following are examples of compositions which can be employed in the method of this invention, which compositions are claimed in the above-cited parent application and patent.

COMPOSITION SUITABLE FOR OPTHALMIC USE a. An aqueous solution of DMSO (5%) and biphenamine hydrochloride (0.1%) can be produced by dissolving 50 grams of the former and 1 gram of the latter in 950 cc of sterile distilled water. The viscosity thereof can be increased with any conventional viscosity enhancing agent, e.g., carboxymethylcellulose.

b. An aqueous solution suitable for opthalmic use of propylene glycol (10%) and biphenamine hydrochloride (0.1%) can be prepared by mixing 100 grams of the former with 900 grams of sterile distilled water containing 1 gram of the latter dissolved therein. The propylene glycol acts as a viscosity enhancing agent, producing a viscous solution.

COMPOSITION 2 a. An opthalmic solution can be formulated in the conventional manner from the following ingredients by first dissolving the biphenamine hydrochloride in the water.

| | |
|---|---|
| Biphenamine.HCl | 1 gm |
| DMSO | 50 cc |
| Sodium biphosphate | 4.0 gm |
| Sodium phosphate | 4.5 gm |
| Sodium chloride | 4.9 gm |
| Benzalkonium chloride | 0.05 gm |
| Water q.s. | 1000 cc | b. The above opthalmic solution can also be prepared with the DMSO omitted therefrom.

COMPOSITION 3 a. An opthalmic ointment can be produced from the following ingredients, by first dissolving the biphenamine hydrochloride in the distilled water.

| | |
|---|---|
| Biphenamine.HCl | 1 gm |
| DMSO | 50 cc |
| Glyceryl monosterate, Acid Type | 180 gm |
| Stearyl alcohol | 50 gm |
| Polysorbate 80 | 20 gm |
| Distilled Water, sterile, q.s. | 1,000 cc | b. An ointment can also be prepared in which the DMSO is replaced by 50 grams of propylene or ethylene glycol.

COMPOSITION 4 a. An opthalmic ointment can be prepared by blending the following sterile ingredients, with the biphenamine hydrochloride first dissolved in the water.

| | |
|---|---|
| Biphenamine.HCl | 100 mg |
| DMSO | 5 gm |
| Ethanol | 10 gm |
| Carbowax 1,500 | 20 gm |
| Distilled Water, sterile q.s. | 100 gm | b. An ointment in which the DMSO is replaced by 10 gm of propylene glycol can similarly be prepared.

COMPOSITION 5 a. A sterile eye drop solution can be produced from the following ingredients, after first dissolving the biphenamine hydrochloride in the water.

| | |
|---|---|
| Biphenamine.HCl | 0.1% |
| DMSO | 5% |
| Sodium borate | 0.1% |
| Benzalkonium chloride | 0.01% |
| Disodium edetate | 0.1% |
| Distilled Water, sterile isotonic | 95 gm | b. Eye drops in which the DMSO is replaced by 7 gm of propylene glycol can also be produced.

In each of the foregoing compositions, the DMSO can be omitted.

The following are examples of the use of the above-compositions, in accordance with the method of this invention.

EXAMPLE 1

A 34 year old male used an unbuffered aqueous solution of biphenamine HCl 0.1% and DMSO 5% as eye drops (1-2 drops per eye) for 2 years on and off to relieve the irritation from his hard contact lenses and Los Angeles smog. He was allergic to the preservative in the saline and artificial tears he had used previously, which prevented their continued use by him. The patient noted a mild stinging which subsided rapidly only when the solution was applied to the eyes when inflammation was present.

For 10 months the patient used the drops daily in the morning. The drops prevented the accumulation of inspissated protein under the contact lenses and prevented or cured the irritation. However after 9 months time the patient beleived his vision in one eye was improved.

Seven years previously, the patient had an accident which broke the orbital bone on the right side of his head and, according to an examination in April 1982 at the University of California, San Diego, resulted in damage to the vitreous of the right eye that was diagnosed as permanent and not curable. Recently, the patient noticed he could see to drive in dense fog, even when the sun caused a glare, and he could see more light than previously. He also had a return of binocular vision.

EXAMPLE 2

A 68 year old male with a history of irritation from contact lenses had macular degeneration of the right eye. He had used many different types of eye drops and had been examined by the same doctor at UCSD who examined the patient described in Example 1. The patient at first noticed a mild irritation to the eye drops but after the inflammation improved, the solution produced no longer caused irritation.

EXAMPLE 3

A 42 year old male had a traumatic accident resulting in a permanently dilated pupil. He had photobia from sun light and could not focus to read because of the permanent dilatation of the pupil of the eye. This was the result of adhesions of the iris and the nonfunction of the ciliary muscle, due to scarring as the result of the trauma. Surgical treatment was recommended and the patient refused. Instead he used the eye drops described in Example 1 daily. Within a week the photophobia disappeared and in two weeks he could read the phone book and small print, which he could not do previously.

Several other human patients and several horses with inflammation of the eyes have responded favorably to these same eye drops.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for preventing or ameliorating an inflammatory response in an eye exposed to a chemical irritant or a contact lense, which comprises applying topically to the affected eye of the patient an anti-inflammatorily effective amount of biphenamine, as an opthomologically acceptable aqueous mixture comprising a pharmaceutically acceptable carrier.

2. A method according to claim 1, wherein the aqueous mixture is about 0.05 to 0.5% solution of a salt of biphenamine in distilled water.

3. A method according to claim 2, wherein the aqueous mixture is about 0.1% solution of biphenamine hydrochloride in distilled water.

4. A method according to claim 1, wherein the aqueous mixture is applied to the affected eye at least once a day on a plurality of successive days.

5. A method according to claim 1, wherein the irritant is a contact lens.

6. A method according to claim 1, wherein the aqueous mixture is about 0.1% solution of biphenamine hydrochloride in water, wherein the irritant is a contact lens, and wherein the aqueous mixture is applied to the affected eye at least once a day on a plurality of successive days.

7. A method according to claim 1, wherein the aqueous mixture comprises up to 10% by weight thereof of DMSO.

8. A method according to claim 7, wherein the biphenamine is present in the aqueous mixture as the hydrochloride salt thereof at a concentration of about 0.05% to 0.5% and the DMSO is present therein at a concentration of about 3% to 7%.

9. A method according to claim 8, wherein the DMSO is present in the mixture at a concentration of about 5% and the biphenamine hydrochloride is present therein at a concentration of about 0.1%.

10. A method according to claim 9, wherein the irritant is a contact lens and the aqueous mixture is applied to the affected eye at least once a day on a plurality of successive days.

* * * * *